United States Patent
Chabin et al.

(10) Patent No.: US 10,762,632 B2
(45) Date of Patent: Sep. 1, 2020

(54) ANALYSIS OF SKELETAL TRAUMA USING DEEP LEARNING

(71) Applicant: Siemens Healthcare GmbH, Erlangen (DE)

(72) Inventors: Guillaume Chabin, Princeton Junction, NJ (US); Zhoubing Xu, Plainsboro, NJ (US); Amitkumar Bhupendrakumar Shah, Fürth (DE); Sasa Grbic, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 87 days.

(21) Appl. No.: 16/128,815

(22) Filed: Sep. 12, 2018

(65) Prior Publication Data

US 2020/0082530 A1 Mar. 12, 2020

(51) Int. Cl.
| | |
|---|---|
| A61B 34/10 | (2016.01) |
| G06T 7/00 | (2017.01) |
| G06T 7/11 | (2017.01) |
| A61B 6/00 | (2006.01) |
| G06K 9/32 | (2006.01) |
| G06K 9/62 | (2006.01) |
| G06T 15/08 | (2011.01) |

(52) U.S. Cl.
CPC ............ *G06T 7/0014* (2013.01); *A61B 6/505* (2013.01); *A61B 6/5217* (2013.01); *A61B 6/5229* (2013.01); *A61B 34/10* (2016.02); *G06K 9/3233* (2013.01); *G06K 9/628* (2013.01); *G06T 7/11* (2017.01); *A61B 2034/105* (2016.02); *G06K 9/6202* (2013.01); *G06K 9/6257* (2013.01); *G06K 2209/055* (2013.01); *G06T 15/08* (2013.01); *G06T 2207/10081* (2013.01); *G06T 2207/20084* (2013.01); *G06T 2207/20221* (2013.01); *G06T 2207/30008* (2013.01)

(58) Field of Classification Search
CPC ....... G06T 7/0012; A61B 6/032; A61B 6/505; A61B 5/0035; A61B 5/4504
See application file for complete search history.

(56) References Cited

U.S. PATENT DOCUMENTS 9,002,081 B2    4/2015  Brown

FOREIGN PATENT DOCUMENTS

KR    101839789 B1    3/2018

OTHER PUBLICATIONS

Dismuke et al., "Clinical Factors and Expenditures Associated with ICD-9-CM Coded Trauma for the U.S. Population: A Nationally Representative Study", Society for Academic Emergency Medicine, Apr. 2017, vol. 24, No. 4, pp. 467-474.
Burns and Traumatic Injury: Fact Sheet, National Institutes of Health; Updated Oct. 2010.
Chong, et al., "Pelvic Fractures and Mortality", The Iowa Orthopaedic Journal, Feb. 5, 2016.

(Continued)

*Primary Examiner* — Sam Bhattacharya (57) ABSTRACT

Systems and methods for determining whether a bone of a patient is injured are provided. A medical image of a bone of a patient is received. A synthesized bone image is generated over the bone in the medical image to provide a reconstructed image. The synthesized bone image represents uninjured bone. The medical image is compared with the reconstructed image to evaluate an injury to the bone of the patient.

20 Claims, 6 Drawing Sheets

(56) References Cited

OTHER PUBLICATIONS

Musculoskeletal Trauma, http://www.imagingpathways.health.wa.gov.au/index.php/imaging-pathways/musculoskeletal-trauma; Retrieved on Sep. 7, 2018, 3 pgs.
Mahendran et al., "Automatic Fracture Detection Using Classifiers—Review", International Journal of Computer Science Issues, vol. 8, Issue 6, No. 1, Nov. 2011, pp. 340-345.
Bandyopadhyay et al., "Long-Bone Fracture Detection in Digital X-ray Images Based on Concavity Index", IWCIA, 2014, LNCS 8466, Springer International Publishing Switzerland, pp. 212-223.
Hachihaliloglu et al., "Automatic Bone Localization and Fracture Detection from Volumetric Ultrasound Images Using 3-D Local Phase Features", Ultrasound in Med & Biol., vol. 38, No. 1, 2012, pp. 128-144.
Drubach et al., "Skeletal Trauma in Child Abuse: Detection with 18F-NaF PET", Radiology: vol. 255: No. 1; Apr. 2010, pp. 173-181.
Ghosh et al., "Automatic Lumbar Vertebra Segmentation from clinical CT for Wedge Compression Fracture Diagnosis", 2011; In Proceedings of SPIE, vol. 7963, 10 pgs.
Wu et al., "Fracture Detection in Traumatic Pelvic CT Images", International Journal of Biomedical Imaging, vol. 2012, 10 pages.
Yang et al., "Automatic Liver Segmentation Using an Adversarial Image-to-Image Network", In International Conference on Medical Image Computing and Computer-Assisted Intervention, pp. 507-515. Springer, Cham, 2017.
Extended European Search Report (EESR) dated Nov. 6, 2019 in corresponding European Patent Application No. 19196603.5.

Generate a skeletal segmentation model from at least one medical image of a bone of a patient
302

↓

Select a region of interest from the skeletal segmentation model
304

↓

Define a mask over the bone in the at least one medical image for the selected region of interest
306

↓

Generate a synthesized bone image portion over the mask in the at least one medical image for the selected region of interest
308

↓

Any remaining regions of interest in the skeletal segmentation model?
310

Yes → (loop back to 304)

No ↓

Combine the synthesized bone image portions to form a synthesized bone image within the mask of the at least one medical image as a reconstructed image
312

↓

Output the reconstructed image
314

ANALYSIS OF SKELETAL TRAUMA USING DEEP LEARNING

BACKGROUND

The present invention relates generally to the analysis of skeletal trauma, and more particularly to the automated detection, quantification, and intervention planning of skeletal trauma using deep learning.

The exposure of the worldwide population to major trauma is consequential. To improve the survival chances of a patient, it is important to quickly and reliably identify injuries with high mortality risk and to accelerate treatment of those identified injuries. In the current clinical practice, a clinician follows diagnostic imaging pathways guidelines to determine anatomies to be scanned and the imaging modalities of the scan. For example, according to diagnostic imaging pathways guidelines, a clinician may analyze computed tomography (CT) images in bone window and in 3D multiplanar reformats to detect bone fractures. To do so, the clinicians identify general patterns on the skeleton to identify fractures and assess the fractures using general standards. Some bones, such as the pelvis or the ribs, are analyzed in more detail and using more specific standards. However, the sheer volume of the whole body CT images and the time pressure to diagnose leads to misdiagnosis or delayed diagnosis of bone fractures, which may result in poor patient outcomes such as physical disability or death.

BRIEF SUMMARY OF THE INVENTION

In accordance with one or more embodiments, systems and methods for determining whether a bone of a patient is injured are provided. A medical image of a bone of a patient is received. A synthesized bone image is generated over the bone in the medical image to provide a reconstructed image. The synthesized bone image represents uninjured bone. The medical image is compared with the reconstructed image to evaluate an injury to the bone of the patient.

In accordance with one or more embodiments, the synthesized bone image is generated using a generative adversarial network.

In accordance with one or more embodiments, the synthesized bone image is generated by generating a skeletal segmentation model from the medical image. For each respective region of interest in a plurality of regions of interest in the skeletal segmentation model, a mask is defined over the bone in the medical image for the respective region of interest and a synthesized bone image portion is generated over the mask in the medical image for the respective region of interest. The synthesized bone image portions for the plurality of regions of interest are combined to form the synthesized bone image.

In accordance with one or more embodiments, comparing the medical image with the reconstructed image comprises determining a score for each respective voxel in the medical image representing differences between the respective voxel in the medical image and a corresponding voxel in the reconstructed image.

In accordance with one or more embodiments, a visual depiction of the degree of injury to the bone may be output based on the score for each respective voxel in the medical image.

In accordance with one or more embodiments, the injury to the bone for one or more respective landmarks of interest may be classified into one of a plurality of bone injury grades based on the score for each voxel in the respective landmark of interest and a plurality of thresholds. The injury to the bone for the one or more respective landmarks of interest may be classified based on an average score or a cumulative score of each voxel in the respective landmark of interest and a plurality of thresholds.

In accordance with one or more embodiments, for a particular landmark of interest of the one or more landmarks of interest, the particular landmark of interest may be evaluated using analysis techniques specific to the particular landmark of interest, the particular landmark of interest determined based on a result of the classifying.

In accordance with one or more embodiments, a clinical therapy may be planned based on results of the analysis techniques specific to the particular landmark of interest.

These and other advantages of the invention will be apparent to those of ordinary skill in the art by reference to the following detailed description and the accompanying drawings.

DETAILED DESCRIPTION

The present invention generally relates to methods and systems for automated detection, quantification, and intervention planning of skeletal trauma using deep learning. Embodiments of the present invention are described herein to give a visual understanding of methods for synthesizing and segmenting multimodal medical images. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while the embodiments discussed herein may be discussed with respect to skeletal trauma in medical images, the present invention is not so limited. Embodiments of the present invention may be applied for the automated detection, quantification, and/or planning for any of measure of interest from any type of image.

Figure 1:
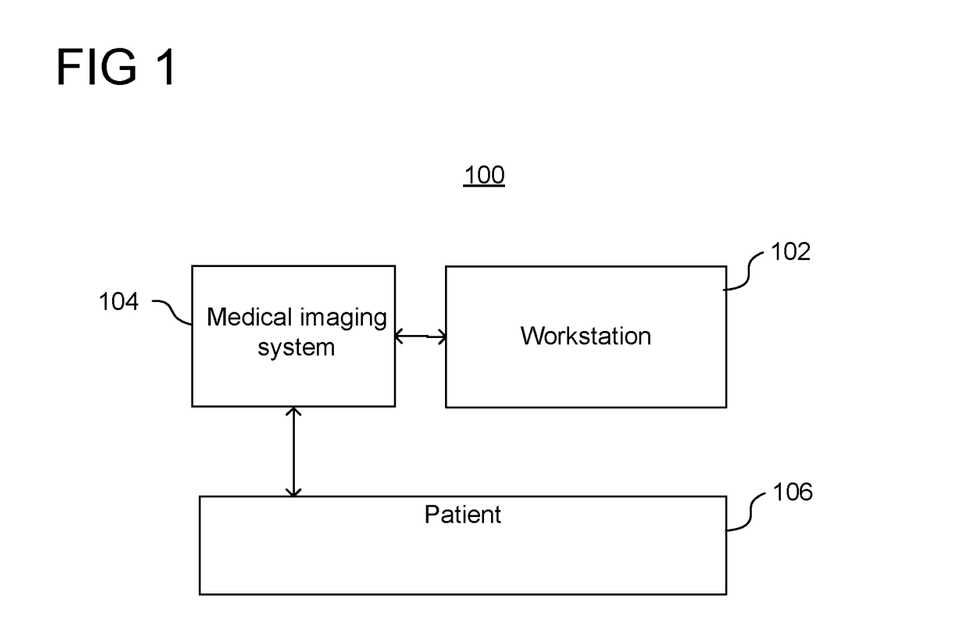
FIG. 1 shows an illustrative system for analyzing medical images, in accordance with one or more embodiments.

FIG. 1 shows a system 100 configured for analyzing medical images, in accordance with one or more embodiments. System 100 includes workstation 102, which may be used for assisting a clinician (e.g., a doctor, a medical professional, or any other user) for performing a medical evaluation on a patient 106 (or any other subject). Workstation 102 may be implemented using any suitable computing device, such as, e.g., computer 602 of FIG. 6.

Workstation 102 may assist the clinician in performing a medical evaluation of patient 106. For example, workstation 102 may receive images of patient 106 from one or more medical imaging systems 104. Medical imaging system 104 may be of any modality, such as, e.g., computed tomography (CT), x-ray, magnetic resonance imaging (MRI), ultrasound (US), single-photon emission computed tomography (SPECT), positron emission tomography (PET), or any other suitable modality or combination of modalities. In another embodiment, workstation 102 may receive the images by loading previously stored images of the patient acquired using medical imaging system 104.

In the current clinical practice, a clinician evaluates a patient for skeletal trauma by manually identifying and quantifying skeletal fractures from medical images. The clinician follows diagnostic imaging pathways guidelines to determine the anatomy of the patient to be imaged and the modality of the images to be acquired. However, such conventional clinical practices may lead to misdiagnosis or delayed diagnosis of bone fractures of the patient, which may result in poor patient outcomes such as physical disability or death.

Embodiments of the present invention provide for the automated detection, quantification, and intervention planning of skeletal trauma using deep learning. In an advantageous embodiment, a reconstructed image is generated by masking bone of a patient in a medical image and generating a synthesized bone image, representing uninjured bone, within the mask. The medical image of the patient is compared with the reconstructed image to evaluate the bone of the patient. Advantageously, embodiments of the present invention provide for the automated detection, quantification, and intervention planning of skeletal trauma in a manner that is faster and more accurate than conventional approaches. Embodiments of the present invention do not require human interaction between data collection and report generation with quantified findings, classifications, and treatment recommendations, thereby reducing the workload of clinicians and allowing them to focus on more critical tasks.

Figure 2:
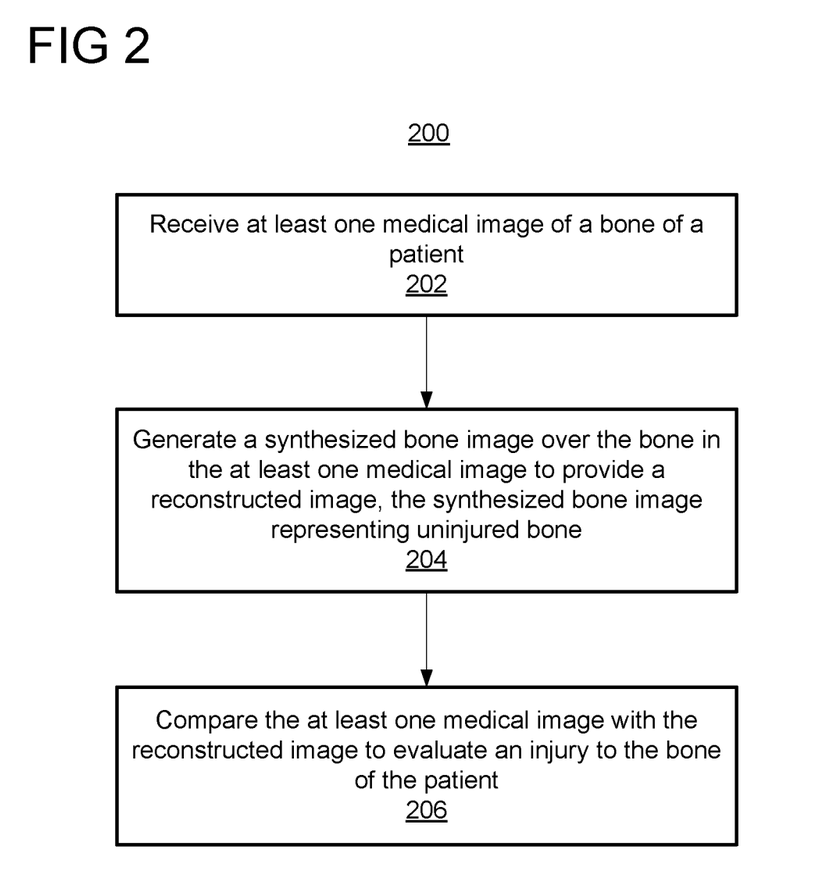
FIG. 2 shows an exemplary method for evaluating an injury of a bone of a patient, in accordance with one or more embodiments.

FIG. 2 shows a method 200 for evaluating an injury of a bone of a patient, in accordance with one or more embodiments. Method 200 may be performed by a computing device, such as, e.g., workstation 102 of FIG. 1.

At step 202, at least one medical image of a bone of a patient is received. In one embodiment, the at least one medical image includes 3D computed tomography (CT) images of an anatomy of interest of the patient. However, it should be understood that the one or more images may be of any suitable modality.

At step 204, a synthesized bone image is generated over the bone in the at least one medical image to provide a reconstructed image for each of the at least one medical image. The synthesized bone image represents uninjured bone. In one embodiment, step 204 is performed by performing the steps of method 300 of FIG. 3, described in more detail below.

At step 206, each of the at least one medical image is compared with its associated reconstructed image to evaluate an injury to the bone of the patient. Evaluating the injury to the bone may include determining whether or not the bone is injured (e.g., fractured), determining a bone injury grade of the bone, or any other suitable evaluation of the bone. The comparison may be performed using any suitable approach.

In one embodiment, each of the at least one medical image is compared with its associated reconstructed image by performing a voxel-by-voxel comparison to determine a difference in intensity values for corresponding voxels in the at least one medical image and the reconstructed image. The comparison may be performed for corresponding voxels in each of the at least one medical image and its associated reconstructed image to determine a score. For example, the score may be a cumulative value of the differences for each voxel in a medical image and a corresponding voxel in its associated reconstructed image (or any other smaller portion within the images), or an average value of the differences for each voxel in a medical image and a corresponding voxel in its associated reconstructed image. A relatively larger score value represents a larger difference between the at least one medical image and the reconstructed image (representing uninjured bone), thereby indicating a higher degree of bone injury. A relatively smaller score value represents a smaller difference between the at least one medical image and the reconstructed image (representing uninjured bone), thereby indicating a lower degree of bone injury.

In one embodiment, landmarks of interest of the bone in the at least one medical image are evaluated. A score may be determined for a portion of the images within the landmarks of interest and classified into one of a plurality of bone injury grades, e.g., based on a plurality of thresholds.

In one embodiment, a skeletal trauma heat map may be generated based on the scores, as described in further detail below with respect to block 504 of FIG. 5.

Figure 3:
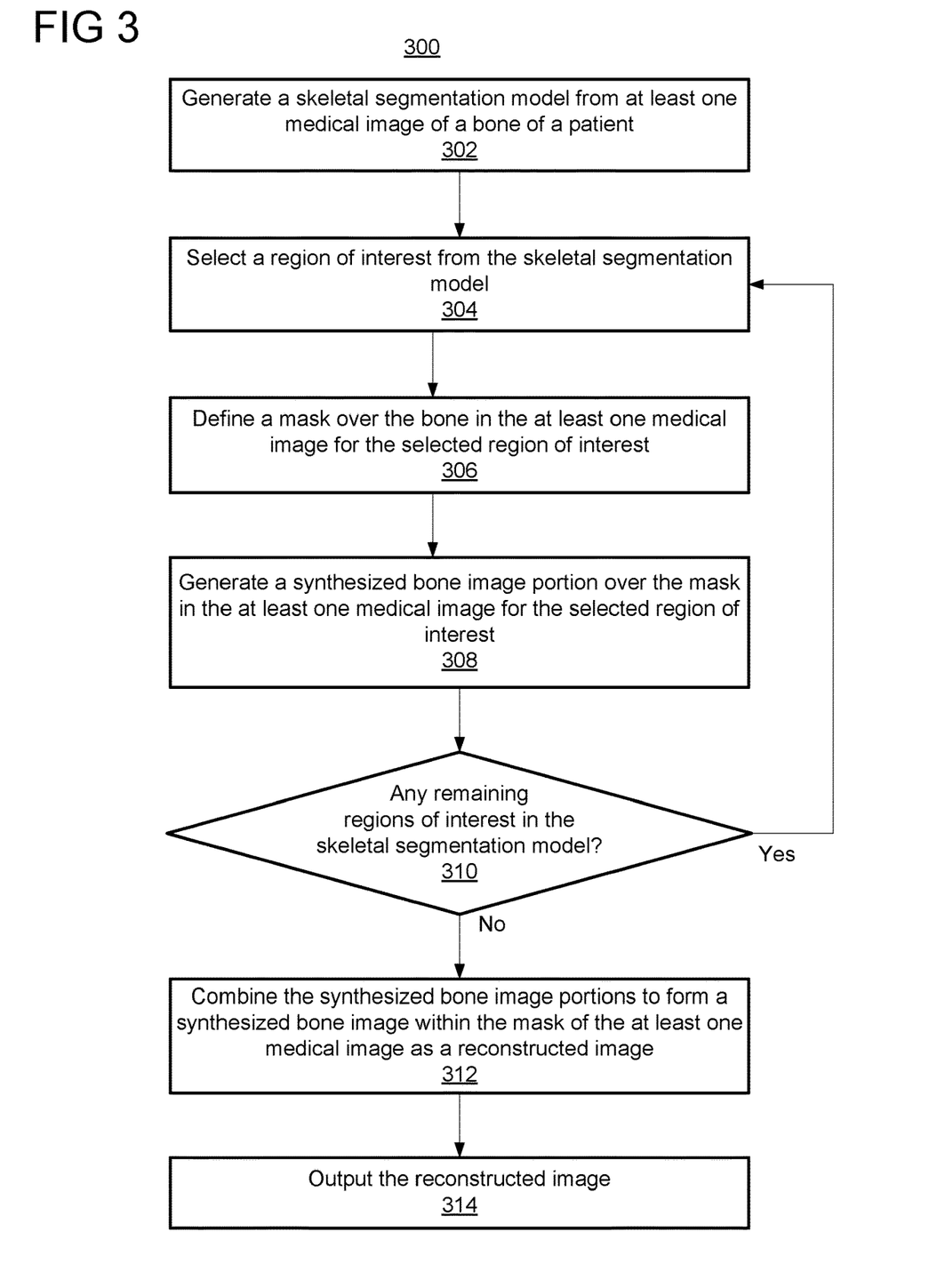
FIG. 3 shows an exemplary method for generating a synthesized bone image over a bone in at least one medical image of a patient, in accordance with one or more embodiments.

FIG. 3 shows a method 300 for generating a synthesized bone image over a bone in at least one medical image of a patient, in accordance with one or more embodiments. In one embodiment, step 204 of FIG. 2 is performed by performing the steps of method 300 of FIG. 3.

At step 302, a skeletal segmentation model is generated from at least one medical image of a bone of a patient. The skeletal segmentation model may be generated using any suitable segmentation technique. In one embodiment, adversarial deep image to image techniques are used to construct a multi-scale 3D skeletal segmentation model using the soft tissue and bone information in the at least one medical image. For example, a discriminative adversarial network may be applied to train deep neural networks to compare segmented shapes of the training images with their respective group truth images. Segmentors trained using deep image to image techniques provide more realistic segmentation masks based on the anatomical shapes. In one embodiment, the segmentators may be trained as described in U.S. Pat. No. 9,760,807, filed Dec. 16, 2016 and issued Sep. 12, 2017, the disclosure of which is incorporated herein by reference in its entirety.

At step 304, a region of interest is selected from the skeletal segmentation model.

At step 306, a mask is defined over the bone (identified at step 302) in the at least one medical image for the selected region of interest. Any suitable technique may be used to mask over the bone in the at least one medical image.

Figure 4:
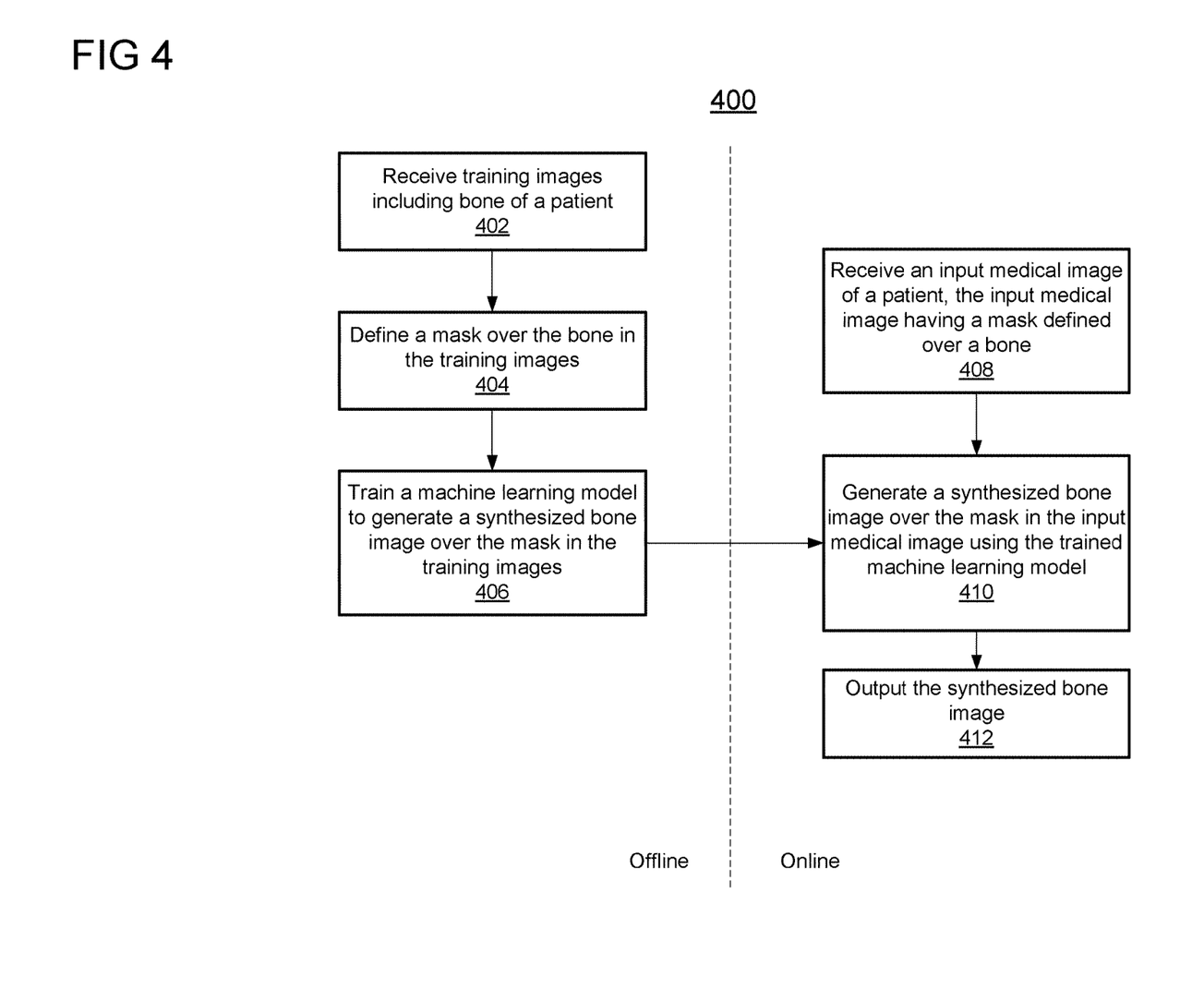
FIG. 4 shows an exemplary workflow for training and applying a machine learning model for generating a synthesized bone image over a mask in at least one medical image, in accordance with one or more embodiments.

At step 308, a synthesized bone image portion is generated over the mask in the at least one medical image for the selected region of interest. The synthesized bone image portion represents uninjured bone. In one embodiment, the synthesized bone image portion is generated using a generative adversarial network (GAN) trained using images of uninjured bones. In one embodiment, step 308 may be performed by performing the steps of workflow 400 of FIG.

4 to train a generator during an offline stage and apply the trained generator during an online stage to generate the synthesized bone image portion over the mask in the at least one medical image, described in detail below.

At step 310, if there are any remaining regions of interest in the skeletal segmentation model, the method returns to step 304 and another region of interest is selected from the skeletal segmentation model. At step 312, if there are no remaining regions of interest in the skeletal segmentation model, the synthesized bone image portions corresponding to each selected region of interest are combined to form a synthesized bone image within the mask of the at least one medical image as a reconstructed image.

At step 314, the reconstructed image is output. In one embodiment, outputting the reconstructed image may include returning the reconstructed image to step 204 of FIG. 2. In some embodiments, the reconstructed image is output by displaying the reconstructed image on a display device of a computer system, storing the reconstructed image on a memory or storage of a computer system, or by transmitting the reconstructed image to a remote computer system.

FIG. 4 shows a workflow 400 for training and applying a machine learning model for generating a synthesized bone image (or a synthesized bone image portion) over a mask in at least one medical image, in accordance with one or more embodiments. Steps 402-406 show an offline or training stage for training a machine learning model. Steps 408-412 show an online or testing stage for applying the trained machine learning model.

At step 402, during an offline stage, training images including bone of a patient are received. The training images are medical images acquired using a medical imaging modality corresponding to the modality of the input image received during the online stage. For example, the modality may be computed tomography (CT), magnetic resonance (MR), DynaCT, ultrasound, x-ray, positron emission tomography (PET), etc. In one embodiment, the training images can be received by loading a number of previously stored medical training images from a database of medical images. In one embodiment, the training images may be selected regions of interest of input training images.

At step 404, a mask is defined over the bone in the training images. The mask may be defined as described above with respect to step 306 of FIG. 3.

At step 406, a machine learning model is trained to generate a synthesized bone image (or a synthesized bone image portion) over the mask in the masked training images. The machine learning model may be trained to generate a synthesized bone image over the mask in the masked training images using the training images received at step 402 as the ground truths.

In one embodiment, a generative adversarial network (GAN) is employed to train the machine learning model. The GAN includes two modules in the form of deep networks: a generator $G_\alpha$ for image generation and a discriminator $D_\beta$ for distinguishing between a real image and a synthesized image. The generator $G_\alpha$ generates a synthesized image $J=G_\alpha(z)$ from the masked training images z. The discriminator $D_\beta$ inputs the synthesized image $J=G_\alpha(z)$ generated by the generator $G_\alpha$ and a real image I (e.g., the training images received at step 402) and classifies each of these images as real or fake (synthesized). During training, the generator $G_\alpha$ and the discriminator $D_\beta$ together play the minimax game of Equation (1), as follows:

$$\min_\alpha \max_\beta E_{I \sim p(I)}[\log(d_\beta(I))] + E_{z \sim p(Z)}[\log(1-D_\beta(J=G_\alpha(z)))], \quad (1)$$

where $\alpha$ and $\beta$ are the parameters (weights) of the generator $G_\alpha$ and discriminator $D_\beta$, respectively. The generator $G_\alpha$ and the discriminator $D_\beta$ evolve dynamically in the sense of learning better network parameters, as long as the game is on until they reach equilibrium; that is, the synthesized image $I=G_\alpha(z)$ becomes indistinguishable (or a close to indistinguishable as possible) from the real image through the eye of the discriminator $D_\beta$. Under such circumstances, the generator essentially generates a real image. The GAN framework enables rapid progress in synthesizing real images.

At step 408, during an online stage, an input medical image of a patient is received. The input medical image has a mask defined over a bone. The input medical image may be received directly from an image acquisition device used to acquire the input medical image, such as, e.g., medical imaging system 104 of FIG. 1. Alternatively, the input medical image may be received by loading a previously acquired medical image from a storage or memory of a computer system or receiving a medical image that has been transmitted from a remote computer system. In one embodiment, the input medical image is a selected region of interest of a medical image. In one embodiment, the input medical image is the at least one medical image having the mask defined over the bone for the selected region of interest from step 306 of FIG. 3.

At step 410, a synthesized bone image (or synthesized bone image portion) is generated over the mask in the input medical image using the trained machine learning model. In one embodiment, the trained machine learning model is the trained generator of the GAN.

At block 412, the synthesized bone image (or synthesized bone image portion) is output. In one embodiment, the synthesized bone image is output by returning the reconstructed image to step 308 of FIG. 3 for a selected region of interest. In some embodiment, the reconstructed image can be output by displaying the reconstructed image on a display device of a computer system, storing the reconstructed image on a memory or storage of a computer system, or by transmitting the reconstructed image to a remote computer system.

It should be understood that once the machine learning model (e.g., the generator) is trained during the training stage, the steps 408-412 of the online stage can be repeated for each newly received input medical image(s). For example, blocks 408-412 can be repeated for each selected region of interest at step 308 of FIG. 3.

Figure 5:
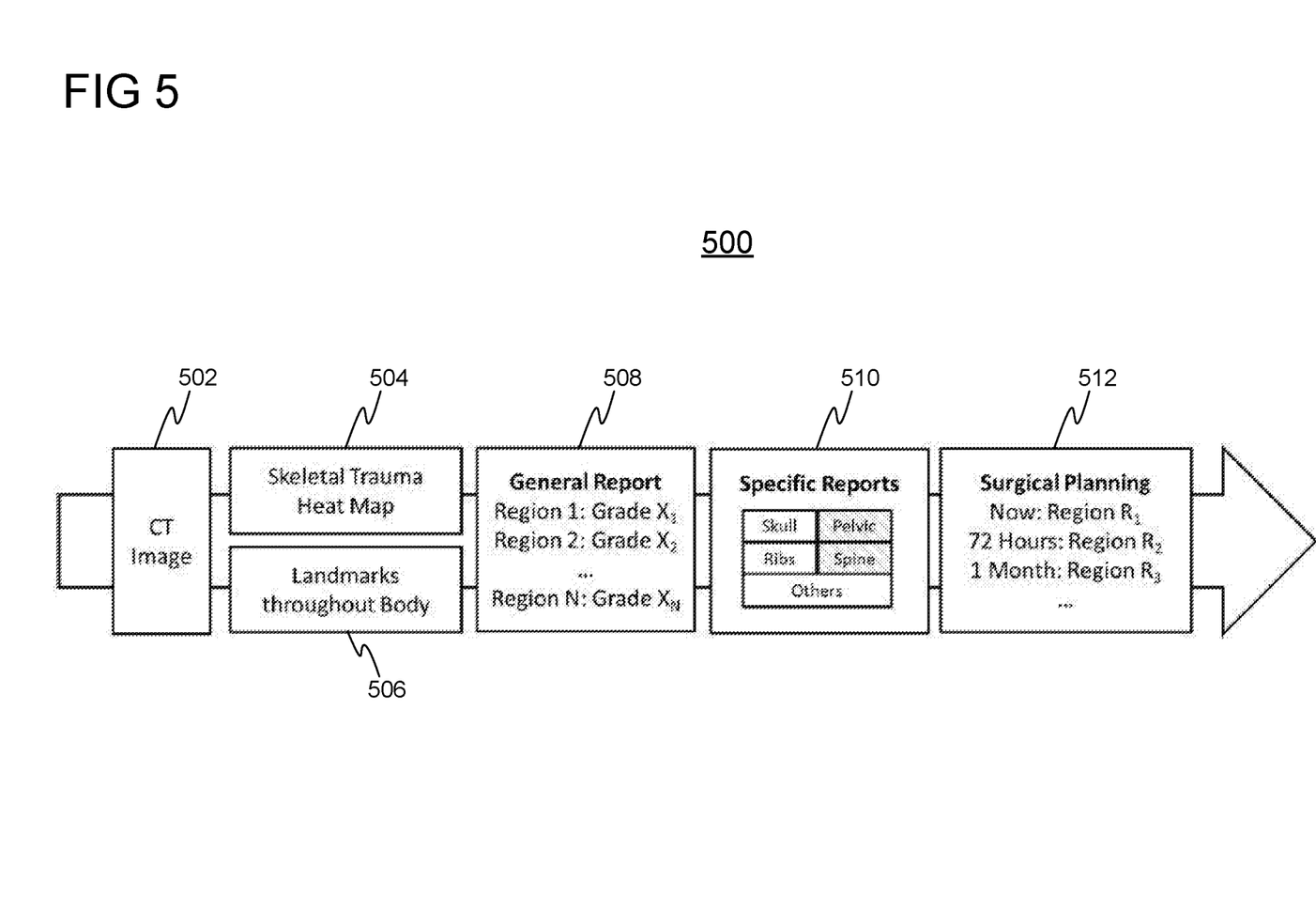
FIG. 5 shows an exemplary workflow for clinical diagnosis and therapy planning of a patient, in accordance with one or more embodiments.

FIG. 5 shows a workflow 500 for clinical diagnosis and therapy planning of a patient, in accordance with one or more embodiments. Workflow 500 may be performed by a computing device, such as, e.g., workstation 102 of FIG. 1.

At block 502, at least one medical image of a bone of a patient is received. The at least one medical image may be of any suitable modality, such as CT.

At block 504, a skeletal trauma heat map is generated. In one embodiment, the skeletal trauma heat map is generated by evaluating an injury of the bone of a patient by performing the steps of method 200 of FIG. 2. In particular, the steps of method 200 are performed to determine a score representing the difference between corresponding voxels in the at least one medical image and the reconstructed image (representing uninjured bone). A relatively larger difference represents a higher degree of bone injury while a relatively smaller difference represents a lower degree of bone injury. The score associated with each voxel is represented on the skeletal segmentation model as a skeletal trauma heat map to provide a visual report showing where the bone of the patient is most divergent from the reconstructed image representing uninjured bone. For example, the score may be visually represented on the skeletal segmentation model by a gradient of color(s) such that a brighter red represents a higher score (i.e., larger difference) and a darker blue represents a lower score (i.e., lower difference). Other approaches for visually representing the score are also contemplated.

At block 506, landmarks of interest are received. The landmarks of interest may be critical regions of the anatomy according to clinically accepted guidelines, as understood by one of ordinary skill in the art. For example, the landmarks of interest may include the pelvis, ribs, spine, skull, etc.

At block 508, a general report is generated and output. The general report may include a bone injury grade associated with one or more landmarks of interest. The bone injury grade may be based on the scores for the one or more landmarks of interest identified on the skeletal trauma heat map. In one embodiment, the scores for the landmarks of interest may be a cumulative score for voxels within the landmarks of interest, an average score for the voxels within the landmarks of interest, etc. The scores may be compared with one or more threshold values to classify the landmarks of interest (e.g., regions) into a bone injury grade. The bone injury grade may range from, e.g., no injury to an open fracture. For example, Region 1 having a score below threshold T1 may be classified with Grade X1, Region 2 having a score between T1 and T2 may be classified with Grade X2, and Region N having a score between T(N−1) and TN may be classified with Grade N. The bone injury grade may represent fracture classifications according to clinical guidelines (e.g., AOSpine). The bone injury grade may be based on, e.g., recommendations for surgery planning, optimizing the survival of the patient, his or her function recovery, and his or her recovery time.

At block 510, specific reports for one or more landmarks of interest are generated based on the general reports for the landmarks of interest. In one embodiment, specific reports are generated for one or more landmarks of interest that are determined to be at risk based on the general reports of the landmarks of interest. For example, landmarks of interest may be determined to be at risk when they are at or above a certain grade, e.g., determined based on clinically accepted guidelines. The specific reports may be generated by applying analysis techniques specific to that landmark of interest. In one embodiment, the analysis techniques specific to landmarks of interest are known techniques.

At block 512, clinical (e.g., surgical) therapy for landmarks of interest may be planned and prioritized based on results of the specific reports. For example, the most critical landmark of interest may be prioritized over the least critical landmark of interest, as determined based on the specific reports. In one embodiment, the clinical intervention may also be planned and prioritized based on information of the patient (e.g., medical records of the patient)

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2-5. Certain steps or functions of the methods and workflows described herein, including one or more of the steps or functions of FIGS. 2-5, may be performed by a server or by another processor in a network-based cloud-computing system. Certain steps or functions of the methods and workflows described herein, including one or more of the steps of FIGS. 2-5, may be performed by a client computer in a network-based cloud computing system. The steps or functions of the methods and workflows described herein, including one or more of the steps of FIGS. 2-5, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2-5, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
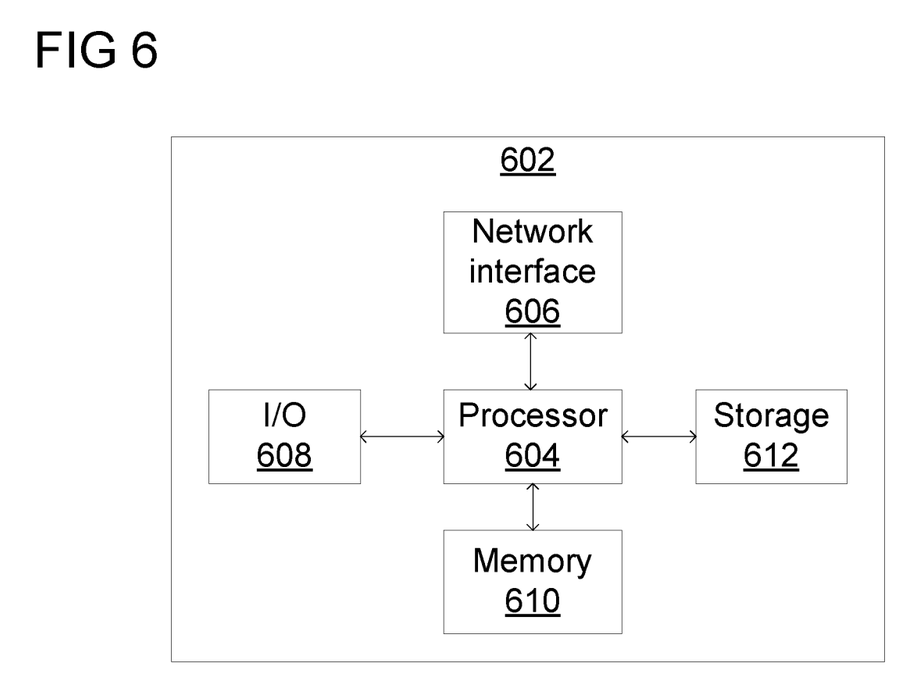
FIG. 6 shows a high-level block diagram of a computer.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIGS. 2-5 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIGS. 2-5. Accordingly, by executing the computer program instructions, the processor 604 executes the method and workflow steps or functions of FIGS. 2-5. Computer 604 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

Any or all of the systems and apparatus discussed herein, including elements of workstation 102 of FIG. 1, may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for determining whether a bone of a patient is injured, comprising:
   receiving a medical image of a bone of a patient;
   generating a synthesized bone image over the bone in the medical image to provide a reconstructed image, the synthesized bone image representing uninjured bone; and
   comparing the medical image with the reconstructed image to evaluate an injury to the bone of the patient.

2. The method of claim 1, wherein generating a synthesized bone image over the bone in the medical image to provide a reconstructed image, the synthesized bone image representing uninjured bone comprises:
   generating the synthesized bone image using a generative adversarial network.

3. The method of claim 1, wherein generating a synthesized bone image over the bone in the medical image to provide a reconstructed image, the synthesized bone image representing uninjured bone comprises:
   generating a skeletal segmentation model from the medical image;
   for each respective region of interest in a plurality of regions of interest in the skeletal segmentation model:
      defining a mask over the bone in the medical image for the respective region of interest, and
      generating a synthesized bone image portion over the mask in the medical image for the respective region of interest; and
   combining the synthesized bone image portions for the plurality of regions of interest to form the synthesized bone image.

4. The method of claim 1, wherein comparing the medical image with the reconstructed image to evaluate an injury to the bone of the patient comprises:
   determining a score for each respective voxel in the medical image representing differences between the respective voxel in the medical image and a corresponding voxel in the reconstructed image.

5. The method of claim 4, further comprising:
   outputting a visual depiction of a degree of injury to the bone based on the score for each respective voxel in the medical image.

6. The method of claim 4, further comprising:
   classifying the injury to the bone for one or more respective landmarks of interest into one of a plurality of bone injury grades based on the score for each voxel in the respective landmark of interest and a plurality of thresholds.

7. The method of claim 6, wherein classifying the injury to the bone for one or more respective landmarks of interest into one of a plurality of bone injury grades based on the score for each voxel in the respective landmark of interest and a plurality of thresholds comprises at least one of:
   classifying the injury to the bone for the one or more respective landmarks of interest into the one of a plurality of bone injury grades based on an average score of each voxel in the respective landmark of interest and a plurality of thresholds; and
   classifying the injury to the bone for the one or more respective landmarks of interest into the one of a plurality of bone injury grades based on a cumulative score of each voxel in the respective landmark of interest and the plurality of thresholds.

8. The method of claim 6, further comprising:

for a particular landmark of interest of the one or more landmarks of interest, evaluating the particular landmark of interest using analysis techniques specific to the particular landmark of interest, the particular landmark of interest determined based on a result of the classifying.

9. The method of claim 8, further comprising:

planning a clinical therapy based on results of the analysis techniques specific to the particular landmark of interest.

10. An apparatus for determining whether a bone of a patient is injured, comprising:

means for receiving a medical image of a bone of a patient;

means for generating a synthesized bone image over the bone in the medical image to provide a reconstructed image, the synthesized bone image representing uninjured bone; and means for comparing the medical image with the reconstructed image to evaluate an injury to the bone of the patient.

11. The apparatus of claim 10, wherein the means for generating a synthesized bone image over the bone in the medical image to provide a reconstructed image, the synthesized bone image representing uninjured bone comprises:

means for generating the synthesized bone image using a generative adversarial network.

12. The apparatus of claim 10, wherein the means for generating a synthesized bone image over the bone in the medical image to provide a reconstructed image, the synthesized bone image representing uninjured bone comprises:

means for generating a skeletal segmentation model from the medical image;

for each respective region of interest in a plurality of regions of interest in the skeletal segmentation model:
means for defining a mask over the bone in the medical image for the respective region of interest, and
means for generating a synthesized bone image portion over the mask in the medical image for the respective region of interest; and means for combining the synthesized bone image portions for the plurality of regions of interest to form the synthesized bone image.

13. The apparatus of claim 10, wherein the means for comparing the medical image with the reconstructed image to evaluate an injury to the bone of the patient comprises:

means for determining a score for each respective voxel in the medical image representing differences between the respective voxel in the medical image and a corresponding voxel in the reconstructed image.

14. The apparatus of claim 13, further comprising:

means for outputting a visual depiction of a degree of injury to the bone based on the score for each respective voxel in the medical image.

15. A non-transitory computer readable medium storing computer program instructions for determining whether a bone of a patient is injured, the computer program instructions when executed by a processor cause the processor to perform operations comprising:

receiving a medical image of a bone of a patient;

generating a synthesized bone image over the bone in the medical image to provide a reconstructed image, the synthesized bone image representing uninjured bone; and comparing the medical image with the reconstructed image to evaluate an injury to the bone of the patient.

16. The non-transitory computer readable medium of claim 15, wherein comparing the medical image with the reconstructed image to evaluate an injury to the bone of the patient comprises:

determining a score for each respective voxel in the medical image representing differences between the respective voxel in the medical image and a corresponding voxel in the reconstructed image.

17. The non-transitory computer readable medium of claim 16, further comprising:

outputting a visual depiction of a degree of injury to the bone based on the score for each respective voxel in the medical image.

18. The non-transitory computer readable medium of claim 16, further comprising:

classifying the injury to the bone for one or more respective landmarks of interest into one of a plurality of bone injury grades based on the score for each voxel in the respective landmark of interest and a plurality of thresholds.

19. The non-transitory computer readable medium of claim 18, wherein classifying the injury to the bone for one or more respective landmarks of interest into one of a plurality of bone injury grades based on the score for each voxel in the respective landmark of interest and a plurality of thresholds comprises at least one of:

classifying the injury to the bone for the one or more respective landmarks of interest into the one of a plurality of bone injury grades based on an average score of each voxel in the respective landmark of interest and a plurality of thresholds; and classifying the injury to the bone for the one or more respective landmarks of interest into the one of a plurality of bone injury grades based on a cumulative score of each voxel in the respective landmark of interest and the plurality of thresholds.

20. The non-transitory computer readable medium of claim 18, further comprising:

for a particular landmark of interest of the one or more landmarks of interest, evaluating the particular landmark of interest using analysis techniques specific to the particular landmark of interest, the particular landmark of interest determined based on a result of the classifying.

* * * * *